United States Patent [19]

Binder et al.

[11] Patent Number: 4,596,830

[45] Date of Patent: Jun. 24, 1986

[54] NOVEL DERIVATIVES OF 2-(2-THIENYL)-IMIDAZO[4,5-B]-PYRIDINES AND THEIR PHARMACEUTICALLY ACCEPTABLE SALTS

[75] Inventors: Dieter Binder, Vienna; Franz Rovenszky, Bruck an der Leitha, both of Austria

[73] Assignee: Laevosan-Gesellschaft m.b.H. & Co. KG, Linz, Austria

[21] Appl. No.: 668,612

[22] Filed: Nov. 2, 1984

[30] Foreign Application Priority Data

Nov. 14, 1983 [AT] Austria ................................. 3999/83

[51] Int. Cl.$^4$ ...................... A61K 31/53; C07D 491/02
[52] U.S. Cl. ...................................... 514/303; 546/118
[58] Field of Search .......................... 546/118; 514/303

[56] References Cited

U.S. PATENT DOCUMENTS 4,336,257  6/1982  Baldwin ............................... 424/256

FOREIGN PATENT DOCUMENTS 49407    4/1982  European Pat. Off. .
72926    3/1983  European Pat. Off. .
2305339  8/1979  Fed. Rep. of Germany .
3225386  1/1984  Fed. Rep. of Germany .
1186504  4/1970  United Kingdom ................ 546/118

OTHER PUBLICATIONS

Hofman, *Imidazole and it's Derivatives*, vol. 1, Interscience Pub. (1953).
March, *Advanced Organic Chemistry*, 1st Ed., McGraw–Hill, 1977, p. 887.
Geiser & Williamson, *Organic Experiments*, 4th Ed., p. 50
*Chemical Abstracts*, vol. 62, 1965, item 4022b, Garmaise et al.

Primary Examiner—Henry R. Jiles
Assistant Examiner—J. Richter
Attorney, Agent, or Firm—Spencer & Frank

[57] ABSTRACT

The invention relates to new therapeutically valuable derivatives of 2-(2-thienyl)-imidazo[4,5-b]pyridines of the general formula

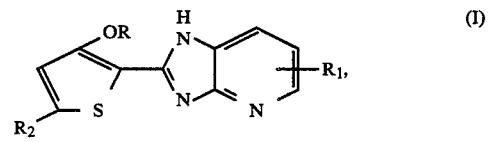

(I)

in which R is methyl or ethyl, $R_1$ is hydrogen or methyl and $R_2$ is methylthio, methylsulfinyl oder methoxy, and their pharmaceutically acceptable acid addition salts, which compounds possess pharmacological properties, especially a positively inotropic activity on the heart.

9 Claims, No Drawings

NOVEL DERIVATIVES OF 2-(2-THIENYL)-IMIDAZO[4,5-B]-PYRIDINES AND THEIR PHARMACEUTICALLY ACCEPTABLE SALTS

SUMMARY OF THE INVENTION

The present invention relates to novel derivatives of 2-(2-thienyl)-imidazo[4,5-b]-pyridines having therapeutical value, a process for the preparation thereof and pharmaceutical compositions containing the same.

The invention relates especially to compounds of the general formula (I)

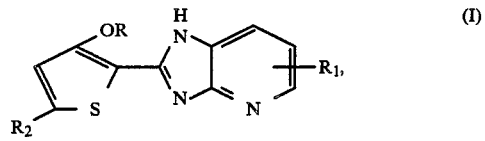

in which R is methyl or ethyl, $R_1$ is hydrogen or methyl and $R_2$ is methylthio, methylsulfinyl or methoxy, and their pharmaceutically acceptable acid addition salts.

The compounds of the above general formula (I) possess valuable pharmacological properties, especially a positively inotropic effect on the heart.

The process of the invention comprises (a) reacting a compound of the general formula (II)

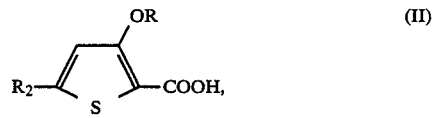

in which R is as defined above and $R_2$ is methylthio or methoxy, with a compound of the general formula (III)

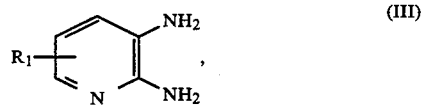

in which $R_1$ is as defined above, in the presence of phosphorous oxychloride or thionylchloride and (b) optionally converting the compound of formula (I) thus obtained, in which $R_2$ is methylthio, with organic peracids or hydrogen peroxide into a compound of the general formula (I), in which $R_2$ is methylsulfinyl, and optionally converting the compound of formula (I) obtained into its pharmaceutically acceptable acid addition salt.

DETAILED DESCRIPTION OF THE INVENTION

The reaction according to process step (a) is conducted with phosphorous oxychloride or thionyl chloride as the dehydrating condensing agent. It is also convenient to use one or both of these compounds as the solvent. The preferred reaction temperature is the reflux temperature of the solvent used.

The preparation of the sulfinyl compounds of general formula (I), according to process step (b), starting from the methylmercapto compounds of general formula (I) obtained, may be conducted with predetermined amounts of organic peracids, e.g. peracetic acid or m-chloroperbenzoic acid, in an inert solvent, e.g. methylene chloride or chloroform, at temperatures of about 0° C. These reactions may also be conducted with predetermined amounts of 30% hydrogen peroxide in glacial acetic acid at room temperature.

The compounds of general formula (I) possess strongly basic properties. Therefore, said compounds may easily be converted into crystalline pharmaceutically acceptable acid addition salts, e.g., the hydrochlorides, which may easily be purified by recrystallization. For that purpose the crude base is dissolved in a suitable solvent, e.g., in a lower alcohol. An equivalent amount of protonic acid is then added, the solvent is evaporated in vacuo and the residue is crystallized from methanol or ethanol, optionally with addition of ether. Suitable examples of such pharmaceutically acceptable salts, in addition to the salt of hydrochloric acid, are the salts of sulfuric acid, nitric acid, phosphoric acid, sulfonic acids, benzoic acid, maleinic acid, tartaric acid and citric acid.

The acid addition salts obtained by the process of the invention have the same high positive inotropic effect as like corresponding free bases of formula (I).

The compounds of formula (III) are known from the literature. The compounds of formula (II) may be prepared starting from compounds of formula (IV), known from the literature, by the following synthesis known to one skilled in the art:

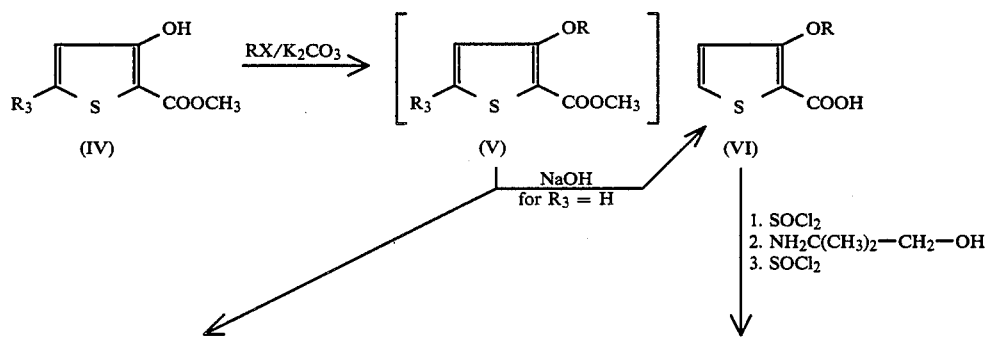

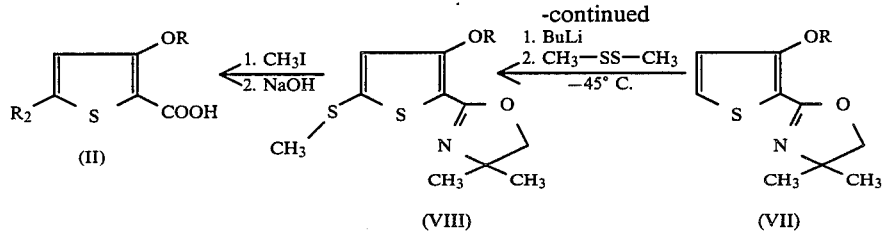

R = CH₃ or C₂H₅
R₂ = methylthio or methoxy
R₃ = hydrogen or methoxy
X = Br, I or O—SO₂—OR The following examples illustrate the present invention:

EXAMPLE 1

2-(3-Methoxy-5-methylthio-2-thienyl)-1H-imidazo[4,5-b]pyridine (formula (I): R=CH₃, R₁=H and R₂=SCH₃)

6.83 g (33.4 mmoles) of 3-methoxy-5-methylthio-2-thiophene carboxylic acid (formula (II): R=CH₃, R₂=SCH₃) are refluxed together with 3.65 g (33.4 mmoles) of 2,3-diaminopyridine (formula III): R₁=H) in 80 ml of phosphorous oxychloride for 3 hours. The reaction mixture obtained is then introduced in portions into about 1.5 l of cold water, stirred well, filtered over Hyflo, made alkaline with potassium carbonate and some ammonia, and extracted several times with methylene chloride. The combined organic phases are dried over sodium sulfate and evaporated. The dark residue is suspended in about 300 ml of methanol, an excess of methanolic hydrochloric acid is added, heated to boiling, activated charcoal is added, filtered, and the solution is concentrated to about 100 ml and allowed to cool. A yellow hydrochloride precipitate of (I) is removed by suction and washed with a small amount of methanol. For preparing the free base, these crystals are suspended in 28 ml of methanol, 1.2 g of a 25% aqueous solution of ammonia are added, 80 ml of water are added, and the yellow crystalline precipitate is removed by suction, washed with water and dried. Yield: 4.24 g (46%), m.p. (ethanol) 224° C. (dec.).

The starting material may be prepared as follows:

3-Methoxy-2-thiophene carboxylic acid (VI: R′=CH₃)

48.5 g (0.31 mmoles) of 3-hydroxy-2-thiophene carboxylic acid methyl ester (IV: R₃=H) are dissolved in 400 ml of acetone, 84.7 g (0.61 moles) of potassium carbonate, 77.3 g (0.61 moles) of dimethylsulfate are added, and the mixture is refluxed with stirring for 1 hour. The salt mass is aspirated, washed several times with acetone and the combined filtrate is concentrated in vacuo. 750 ml of aqueous 2N sodium hydroxide are added and boiled. The reaction solution is cooled, washed with ether and acidified with concentrated HCl. The precipitating colorless crystals are aspirated and recrystallized from ethanol. Yield: 43.1 g (89%), m.p. 184°-185° C.

3,4-Dihydro-4,4-dimethyl-2-(3-methoxy-2-thienyl)-oxazole (VII: R=CH₃)

50.2 g (0.32 moles) of 3-methoxy-2-thiophene carboxylic acid are refluxed in 300 ml of thionyl chloride for 2 hours, the reaction solution is evaporated in vacuo, the crystalline residue (56 g) is dissolved in 250 ml of methylene chloride and added dropwise with stirring to a solution of 57 g (0.64 moles) of 2-amino-2-methyl-1-propanol in 200 ml of methylene chloride at 0° C. within ½ hour. After 12 hours of stirring at room temperature, the solution is concentrated under vacuum, cooled, the precipitate is aspirated, washed well with water, dried, 135 ml of thionyl chloride are added slowly with cooling, and the solution is stirred at room temperature for 12 hours. Then it is evaporated in vacuo, the residue is dissolved in water, extracted with ether, the aqueous phase is made alkaline with aqueous 2N sodium hydroxide and extracted several times with methylene chloride. The combined methylene chloride phases are dried with sodium sulfate and evaporated in vacuo. Yield: 57.0 g (84%), m.p. (petroleum ether) 97°-98° C.

3,4-Dihydro-4,4-dimethyl-2-(3-methoxy-5-methylthio-2-thienyl)-oxazole (VIII: R=CH₃)

27 g (0.128 moles) of 3,4-dihydro-4,4-dimethyl-2-(3-methoxy-2-thienyl)-oxazole are dissolved in 400 ml of absolute tetrahydrofuran, the solution is cooled to −45° C. and 88 ml (0.141 moles) of a 1.6 molar solution of butyllithium in n-hexane is added dropwise such that the temperature in the reaction mixture does not exceed −45° C. After completion of the addition it is stirred further for 1.5 hours at −45° C., a solution of 13.9 g (0.147 moles) of dimethylsulfide in 70 ml of absolute tetrahydrofuran is added and stirring continues for an additional 30 minutes at this temperature. Then it is heated to −20° C., poured onto water and extracted several times with ether. The combined ether phases are dried with sodium sulfate, decolored with activated charcoal, evaporated in vacuo and the crystalline residue is recrystallized from petroleum ether. Yield: 24.7 g (75%), m.p. 56°-58° C.

3-Methoxy-5-methylthio-2-thiophene carboxylic acid (II: R=CH₃, R₂=SCH₃)

250 ml of methyl iodide are added to 24.2 g (0.094 moles) of 3,4-dihydro-4,4-dimethyl-2-(3-methoxy-5-methylthio-2-thienyl)-oxazole and stirred at room temperature for 12 hours. The excess of methyl iodide is then distilled off, 350 ml of aqueous 1N sodium hydroxide are added to the crystalline residue, stirred at room temperature for a further 12 hours, the reaction mixture is diluted with water until the yellow precipitate dissolves, extracted with ether, the aqueous phase acidified with concentrated hydrochloric acid and the precipitating colorless crystals are aspirated, washed with water and dried. Yield: 15.8 g (82%), m.p. (CCl₄) 126°-128° C. (dec.).

EXAMPLE 2

2-(3-Methoxy-5-methylsulfinyl-2-thienyl)-1H-imidazol[4,5-b]pyridine (I: $R=CH_3$, $R_1=H$ and $R_2=SO-CH_3$)

3.80 g (13.7 mmoles) of the 2-(3-methoxy-5-methylthio-2-thienyl)-1H-imidazo[4,5-b]pyridine, obtained in Example 1, are dissolved in 80 ml of glacial acid, 1.63 g (14.4 mmoles) of 30% aqueous solution of hydrogen peroxide are added and stirred at room temperature for 30 hours. The solution is concentrated in vacuo, the residue is dissolved in a small amount of water, neutralized with a saturated solution of sodium hydrogen carbonate, and the precipitating crystals are aspirated and dried. Yield: 3.95 g (98%), m.p. (ethanol) 233°-235° C. (dec.).

EXAMPLE 3

2-(3,5-Dimethoxy-2-thienyl)-1H-imidazo[4,5-b]-pyridine (formula (I): $R=CH_3$, $R_1=H$ and $R_2=OCH_3$)

The reaction of 3,5-dimethoxy-2-thiophene carboxylic acid (formula (II): $R=CH_3$, $R_2=O-CH_3$) in a manner analogous to Example 1 provides the title compound in a yield of 29% in the form of yellowish crystals. If desired, it can be recrystallized from ethanol, m.p. 93°-96° C.

The starting material may be prepared as follows:

Methyl ester of 3,5-Dimethoxy-2-thiophene carboxylic acid 8.0 g (0.0425 moles) of the methylester of 3-hydroxy-5-methoxy-2-thiophene carboxylic acid, 6.5 g (0,0468 moles) of potassium carbonate and 5.9 g (0.0468 moles) of dimethyl sulfate are refluxed in 100 ml of acetone for 1 hour. Subsequently the reaction mixture is evaporated, the residue is partitioned between water and diethyl ether, and the aqueous phase is extracted three times with a total amount of 200 ml of diethyl ether. The organic phase is dried over sodium sulfate/activated charcoal and evaporated. Yield: 8.62 g of yellowish crystals (99.8% of theory), m.p. 62°-64° C. (petroleum ether).

3,5-Dimethoxy-2-thiophene carboxylic acid 10.0 g (0.0492 moles) of the methyl ester of 3,5-dimethoxy-2-thiophene carboxylic acid are refluxed in 80 ml of 2N NaOH for 1 hour. It is then cooled to 0° C., diluted with a small amount of cold water and acidified dropwise with concentrated HCl to pH 1.5. It is stirred for a short period, the precipitated crystals are aspirated, washed with cold water and a small amount of cold methanol, and quickly suctioned dry. The crystals are dried at 20° C./2 mbar. Yield: 4.2 g of colorless crystals (45.4% of theory), m.p. 135° C. (dec.) (MeOH).

EXAMPLE 4

2-(3-Methoxy-5-methylsulfinyl-2-thienyl)-1H-imidazo[4,5-b]pyridine hydrochloride 3.0 g (10.8 mmoles) of the 2-(3-methoxy-5-methylsulfinyl-2-thienyl)-1H-imidazo[4,5-b]pyridine obtained in Example 2 are suspended in 80 ml of methanol and 14 ml of 1N methanolic hydrochloric acid are added. It is then evaporated to dryness in vacuo and the residue is recrystallized from ethanol. Yield: 3 g (95.5%) of yellow crystals, m.p. 210° C. (dec.).

In analogous manner there are obtained:

2-(3-methoxy-5-methylthio-2-thienyl)-1H-imidazo[4,5-b]pyridine hydrochloride, m.p. 217° C. (dec.).

2-(3,5-dimethoxy-2-thienyl)-1H-imidazo[4,5-b]pyridine hydrochloride, m.p. 145° (dec.).

As mentioned above, the compounds of the invention possess valuable pharmacological properties, especially a positive inotropic activity on heart muscle, which is demonstrated in the following by means of a representative compound of the invention, namely 2-(3-methoxy-5-methylsulfinyl-2-thienyl)-1H-imidazo[4,5-b]pyridine hydrochloride (obtained according to Example 4).

Said compound was tested both in vitro in isolated, perfused, spontaneously beating hearts of guinea pigs and rats and in vivo in rats with respect to their haemodynamic activity.

The tested compound had a positive inotropic effect on the hearts of both species similar to the glycoside Quabain. In a dosage of $6 \times 10^{-6}M$, surprisingly, the left-ventricular pressure development was increased by 130%, and the maximum rate of increase of pressure increased by about 120%. In the presence of the test compound, no impairment of the mycardial oxygen supply was observed.

In vivo the following haemodynamic parameters were determined in a rate under inactin ®-anesthesia through a special ultraminiatur-catheter tipped manometer: heart frequency, left-ventricular systolic pressure (LVSP), and the increased rate of the left ventricular pressure (LV dP/dt max). (Method described in Zimmer, H.-G.: Basic Research Cardiol. 78, 77–84, 1983).

The tested range of doses was between 0.1 mg/kg and 20 mg/kg/hour. The in vivo assay confirmed the positive inotropic effect found in vitro.

In the following table the results of two representative experiments are reported.

| dosage 20 mg/kg/hour | heart frequency (beats/min) | LV dP/dt max (mm Hg/s) | LVSP (mm Hg) |
| --- | --- | --- | --- |
| before application | 316 | 6,769 | 143 |
| after application | 440 | 10,154 | 129 |
| before application | 336 | 5,230 | 136 |
| after application | 992 | 12,600 | 136 |

It has been noted that the positive inotropic effect was still present after discontinuation of the infusion for a relatively long period.

Summarizing, it can be said that from the therapeutical aspect 2-(3-methoxy-5-methylsulfinyl-2-thienyl)-1H-imidazo[4,5-b]pyridine hydrochloride is a highly interesting substance for the treatment of myocardial insufficiency, and could be a substitute for the highly toxic glycosides.

What is claimed is:

1. 2-(2-Thienyl)-1H-imidiazo[4,5-b]pyridines of the general formula (I)

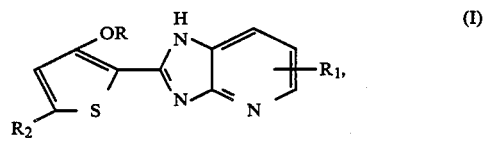

in which R is methyl or ethyl, $R_1$ is hydrogen or methyl and $R_2$ is methylthio, methylsulfinyl or methoxy, and their nontoxic, pharmaceutically acceptable acid addition salts having a positive inotropic effect on heart muscle.

2. 2(3-Methoxy-5-methylthio-2-thienyl)-1H-imidazo[4,5-b]-pyridine and the hydrochloride thereof.

3. 2-(3-Methoxy-5-methylsulfinyl-2-thienyl)-1H-imidazo[4,5-b]pyridine and the hydrochloride thereof.

4. 2-(3,5-Dimethoxy-2-thienyl)-1H-imidazo[4,5-b]pyridine and the hydrochloride hereof.

5. A composition of matter comprising a compound according to claim 1, in an effective amount for having a positive inotropic effect on heart muscle together with a pharmaceutically acceptable carrier or diluent.

6. A composition of matter comprising a compound according to claim 2, in an effective amount for having a positive inotropic effect on heart muscle together with a pharmaceutically acceptable carrier or diluent.

7. A composition of matter comprising a compound according to claim 3, in an effective amount for having a positive inotropic effect on heart muscle together with a pharmaceutically acceptable carrier or diluent.

8. A composition of matter comprising a compound according to claim 4, in an effective amount for having a positive inotropic effect on heart muscle together with a pharmaceutically acceptable carrier or diluent.

9. A nontoxic, pharmaceutically acceptable acid addition salt of the compound of claim 1, having a positive inotropic effect on heart muscle, selected from the acid addition salts of hydrochloric acid, sulfuric acid, nitric acid, phosphoric acid, sulfonic acid, benzoic acid, maleinic acid, tartaric acid and citric acid.

* * * * *